(12) United States Patent
Köhler et al.

(10) Patent No.: US 11,561,189 B2
(45) Date of Patent: Jan. 24, 2023

(54) DEVICE FOR DETERMINING THE MOISTURE AND/OR THE CONDUCTIVITY OF A MEDIUM

(71) Applicant: Imko Micromodultechnik GmbH, Ettlingen (DE)

(72) Inventors: Kurt Köhler, Ettlingen (DE); Timo Camek, Karlsruhe (DE)

(73) Assignee: IMKO Micromodultechnik GmbH, Ettlingen (DE)

( * ) Notice: Subject to any disclaimer, the term of this patent is extended or adjusted under 35 U.S.C. 154(b) by 310 days.

(21) Appl. No.: 16/765,843

(22) PCT Filed: Nov. 13, 2018

(86) PCT No.: PCT/EP2018/081029
§ 371 (c)(1),
(2) Date: May 20, 2020

(87) PCT Pub. No.: WO2019/096766
PCT Pub. Date: May 23, 2019

(65) Prior Publication Data
US 2020/0355638 A1    Nov. 12, 2020

(30) Foreign Application Priority Data
Nov. 20, 2017   (DE) ..................... 10 2017 127 286.0

(51) Int. Cl.
*G01R 27/04* (2006.01)
*G01K 13/02* (2021.01)
(Continued)

(52) U.S. Cl.
CPC ........... *G01N 27/048* (2013.01); *G01K 13/02* (2013.01); *G01N 27/043* (2013.01); *G01N 33/025* (2013.01)

(58) Field of Classification Search
CPC ....... G01F 23/284; G01F 23/26; G01N 22/00; G01N 9/24; G01N 27/048; G01N 27/043;
(Continued)

(56) References Cited

U.S. PATENT DOCUMENTS

2003/0079365 A1* 5/2003 Corak ..................... F26B 9/063
34/524
2015/0177163 A1* 6/2015 Edvardsson ............. G01N 9/24
324/642
(Continued)

FOREIGN PATENT DOCUMENTS

DE      102004032965 A1    2/2006
DE      102004035757 B3    5/2006
(Continued)

*Primary Examiner* — Lee E Rodak
(74) *Attorney, Agent, or Firm* — Kelly J. Smith; Endress+Hauser (USA) Holding, Inc.

(57) ABSTRACT

The invention includes a device for determining the moisture or conductivity of a medium in a container. A measurement probe is plunged into the medium and consists of a conductive material, a conductive rod, and a first feed-through component designed such that the conductive rod can be fastened to an electrically conductive wall or holder. A rod of a non-conductive material and a second feed-through component are provided, where the non-conductive rod can be fastened to the wall, the conductive rod and the non-conductive rod are dimensioned and oriented that the measurement probe is oriented parallel to the longitudinal axis of the container and a signal-processing unit designed such that high-frequency measurement signals are conducted via the measurement line to the measurement probe and that the moisture or the conductivity of the medium is determined by means of a TDR method.

12 Claims, 5 Drawing Sheets

(51) Int. Cl.
*G01N 27/04* (2006.01)
*G01N 33/02* (2006.01)

(58) Field of Classification Search
CPC .................. G01N 33/025; G01N 33/46; G01N 2033/245; G01N 27/02; G01R 27/02; G01R 27/26; G01R 27/2605; G01K 13/02
See application file for complete search history.

(56) References Cited

U.S. PATENT DOCUMENTS

| | | | |
|---|---|---|---|
| 2016/0003662 A1* | 1/2016 | Dayal | G01R 27/02 73/304 R |
| 2016/0169720 A1* | 6/2016 | Xie | G01N 22/00 73/861.11 |

FOREIGN PATENT DOCUMENTS

| | | | |
|---|---|---|---|
| DE | 102012112318 A1 | 6/2014 | |
| EP | 2741059 B1 | 7/2016 | |

* cited by examiner

DEVICE FOR DETERMINING THE MOISTURE AND/OR THE CONDUCTIVITY OF A MEDIUM

CROSS-REFERENCE TO RELATED APPLICATIONS

The present application is related to and claims the priority benefit of German Patent Application No. 10 2017 127 286.0, filed on Nov. 20, 2017 and International Patent Application No. PCT/EP2018/081029 filed on Nov. 13, 2018, the entire contents of which are incorporated herein by reference.

TECHNICAL FIELD

The invention relates to a device for determining the moisture and/or conductivity of a flowable medium in a container.

BACKGROUND

Planar moisture sensors having a plurality of measurement lines have become known for measuring the moisture of media. Either microwaves are used in planar moisture sensors or planar moisture sensors operate on the basis of the capacitive measurement principle. In the known planar sensors, the medium to be measured comes into direct contact with the sensing element. This is disadvantageous, especially, if the moisture of very heterogeneous materials, such as corn cobs or wood chips, is to be determined. The size of the measuring field is limited since the medium to be measured is not located between the two or three measurement lines but above the two or three planar measurement lines. Deposits or a water film can also form on the surface of the sensing element, which of course is not conducive to the measurement accuracy of the planar moisture sensors.

A method as well as a device for determining the moisture of a product/medium via a TDR method, i.e., the transit time of high-frequency measurement signals, has become known from EP 0 478 815 A1. In the known method, a rectangular signal is applied to a measurement line by means of a measurement signal transmitter. The pulse duration of the signal is in this case selected to be twice as large as the transit time of the signal on the measurement line. The signal is reflected by the measurement line, i.e., at the end of the measurement line. The sum signal is thus formed at the input of the measurement line or at the output of the measurement signal transmitter by superimposing the amplitudes of the measurement signal fed into the measurement line and of the measurement signal reflected by or at the end of the measurement line. The measurement line is preferably designed as a probe.

In the TDR method, it must be ensured that an electrical pulse can propagate along the measurement line/probe and be reflected at the end of the measurement line/probe. The moisture of the medium is determined from the transit time of the pulse. In the known solution, the pulse, triggered by the signal processing unit, runs through a cable to the first measurement line, from the end of the first measurement line to the beginning of the second measurement line, is reflected at the end of the second measurement line and runs back to the signal processing unit. The transit time of the pulse is used to calculate the moisture value and is output via standard analog signals which are based, for example, on the 0-20 mA or the 4-20 mA standard. However, the moisture can also be output in parallel via a digital interface, such as an RS 485.

Although the known method as well as the known 2-rod or 3-rod TDR probes provide good results, they have the disadvantage that in the case of rod probes having a plurality of parallel rods, the spacings of the individual rods and the thickness of the rods influence the medium and the measurement. If the rods are thick and the spacing of the rods is relatively small, this can significantly interfere with the flow behavior of the medium to be measured in a container, especially, during filling or emptying. A relatively large total surface area of a plurality of thicker rods represents a considerable resistance which must be overcome by the flowable, moving medium. In the extreme case, the medium can even clump between the rods. In addition, the rods generally consist of solid steel material, which entails the risk of the rods bending during filling as a result of strong mechanical loading. It also cannot be ruled out that the rods may break in some circumstances.

DE 20 2013 102 514 U1 discloses a TDR fill level measuring device for determining the fill level of a filling medium in a container. This fill level measuring device is designed such that it also supplies information about the moisture of the filling medium in addition to the fill level information. Both process variables are determined based on the echo curve of the measurement signal, where the echo curve represents the amplitude of the measurement signal plotted against the transit time or the travel path. The measurement accuracy of the known solution is insufficient for moisture determination of agricultural products, such as corn cobs.

A rod-shaped TDR measurement probe of the applicant for determining the moisture and/or conductivity of, especially, coarse-grained products, such as grains, corn cobs, wood chips, oil-containing fruits, etc., which are stored in a container has become known under the name Trime-GW. The rod-shaped TDR measurement probe made of electrically conductive material is fastened to the inner wall of the container by holders made of glass fibers. It is arranged and oriented in such a way that it is in contact with the medium to be measured during the measurement operation. The signal processing unit, which generates the high-frequency measurement signals and determines the moisture or the conductivity based on the measured data, is arranged outside the container. The measurement signals are fed into the measurement probe through a flexible cable between the signal processing unit and one of the two end regions of the rod-shaped measurement probe.

An application of a TDR measurement probe or a plurality of TDR measurement probes for determining the moisture of porous agricultural products is described in U.S. Pat. No. 6,747,461 b1. In this application, the information provided by the TDR measurement probes scattered around inside the container is used to control a drying system in such a way that the drying process of the agricultural product in the container takes place in an optimal manner.

SUMMARY

The object of the invention is to disclose a break-resistant device for determining the moisture and/or conductivity.

The object is achieved by a device for determining the moisture and/or the conductivity of a (flowable) medium in a container, comprising a measurement probe of a specified length which is plunged into the medium, wherein the measurement probe consists of a conductive material. A measurement line designed as a conductive rod is provided in the upper end region of the measurement probe. Furthermore, a first feed-through or a first fastening component is provided, which is designed in such a way that the conductive rod formed as the measurement line can be fastened, in an electrically insulated manner, to the electrically conductive wall of the container or to an electrically conductive elongate holder. A rod of a non-conductive material is provided in the lower end region of the measurement probe. Furthermore, a second feed-through or a second fastening component is provided, which is designed in such a way that the non-conductive rod can be fastened to the wall of the container or to the elongate holder. The conductive rod and the non-conductive rod are dimensioned and oriented such that the measurement probe, when mounted, is oriented substantially in parallel to the longitudinal axis of the container or the elongate holder. High-frequency measurement signals are conducted via the measurement line to the measurement probe by a signal processing unit, and the moisture and/or conductivity of the medium is/are determined by means of a TDR method. Similar measuring methods are known from the prior art.

The device according to the invention is best suited for determining the moisture and/or conductivity of a medium. The medium may be a bulk heterogeneous material (e.g., corn cobs) or a low-density medium, e.g., steam and gas. The measuring field is constructed between the measurement rod, the measurement probe and a metal wall of the container or of the holder on which the device according to the invention is mounted for measuring purposes. The device according to the invention can thus be used for large measurement volumes, for example, in grain silos. Due to the design of the individual components of the device according to the invention, it is break-resistant even under extreme mechanical loading.

According to an advantageous development of the device according to the invention, it is provided that the conductive rod configured as a measurement line and the non-conductive rod are dimensioned such that a measuring field assigned to the high-frequency measurement signal is constructed between the conductive rod, the measurement probe and the adjoining surface of the inner wall of the container or holder.

Furthermore, it is proposed that the measurement probe and the conductive rod designed as a measurement line preferably consist of a flexible carrier, especially, a glass fiber carrier, the flexible carrier being surrounded by a thin-walled, electrically conductive tube. It is further proposed that a glass fiber carrier is, especially, a cross-wound glass fiber rod. Alternatively, it is provided that the glass fiber carrier be provided with a conductive coating on the outer surface. The advantage of this design is that the measuring device according to the invention is characterized by a high break resistance. Even when very large mechanical loads are applied, including shock loads, there is no risk that the components in contact with the contents of the container break or are torn off. After the load disappears, the measuring device resumes its original shape.

The thickness of the thin-walled, electrically conductive tube or of the coating is preferably in the range of 0.5 to 2.5 mm, preferably 1 mm. The outer diameter of the thin-walled, electrically conductive tube or of the coating is between 5 and 15 mm, preferably 10 mm. Alternatively to the electrically conductive tube or the electrically conductive coating, an electrically conductive shrink tube can also be drawn over the glass fiber carrier.

According to an advantageous embodiment of the device according to the invention, the non-conductive rod is also designed as a flexible glass fiber rod to ensure break resistance.

According to an advantageous development of the device according to the invention, the conductive rod configured as a measurement line and the non-conductive rod have an overall length which is preferably between 0.3 and 1.2 m.

With regard to the first feed-through or the first fastening component and the second feed-through or the second fastening component, it is proposed that they consist of an insulating plastic or of an insulating ceramic, the ceramic preferably being used when high temperatures prevail in the container.

In addition, it is considered to be particularly advantageous if a cable, especially, a coaxial cable, is provided by which the signal processing unit is electrically connected to the end region of the conductive rod designed as a measurement line. It is additionally proposed that a twisted wire is used as the cable. Twisted wires have higher impedance (100-150Ω) than coaxial cables.

As already stated above, the device can be attached to the wall of a container so that the sensor components, i.e., especially, the single-rod probe formed by the measurement probe and the conductive rod, are in contact with the medium to be measured. An alternative proposes that a rail configured as a holder is used instead of the wall of the container. This rail is preferably configured as a U-shaped metal rail. The measurement probe is arranged on the outer surface of the central section of the rail, while the signal processing unit is arranged on the inner surface of the central section of the rail.

In addition, it is considered to be very advantageous if the holder and the single-rod probe form a compact unit. Especially, such an embodiment makes it very easy to attach several of the compact single-rod probes in a cascade to an elongate fastening rail. This makes it possible to produce a moisture profile of the medium from the height or a desired partial height of the container. Furthermore, fastening means for fastening the fastening rail to the floor and to the cover of the container are provided in the end regions of the elongate fastening rail. These fastening means are designed in such a way that the measuring device according to the invention is stably anchored in the container.

It is furthermore provided that each compact single-rod probe is assigned a temperature sensor. If the temperature in the vicinity of the measurement probe is known, the influence of temperature on the measurement of the moisture or conductivity can be compensated for. This increases the measurement accuracy of the measuring device.

A further embodiment of the device according to the invention provides that the container, which is metallic or electroconductive at least on the inner surface, is configured as a pipeline section. The single-rod probe is installed in the pipeline section, preferably in such a way that the measurement probe is mounted along the longitudinal axis of the pipeline section. This embodiment is preferably used for measuring the conductivity or moisture or the water content in a low-density medium. The medium 5 is, for example, hot steam or a gas.

The design is in principle comparable to the design of a coaxial cable. The electrical measuring field of the TDR signal is constructed between the single-rod probe and the inner metallic surface of the pipe. The break-resistant design of the probe arrangement has a positive effect on possible pressure surges occurring in the pipeline. In high-temperature applications, the insulating components of the single-rod probe are made of ceramic rather than plastic.

BRIEF DESCRIPTION OF THE DRAWINGS

The invention is explained in more detail with reference to the following figures. These show.

DETAILED DESCRIPTION

Figure 1:
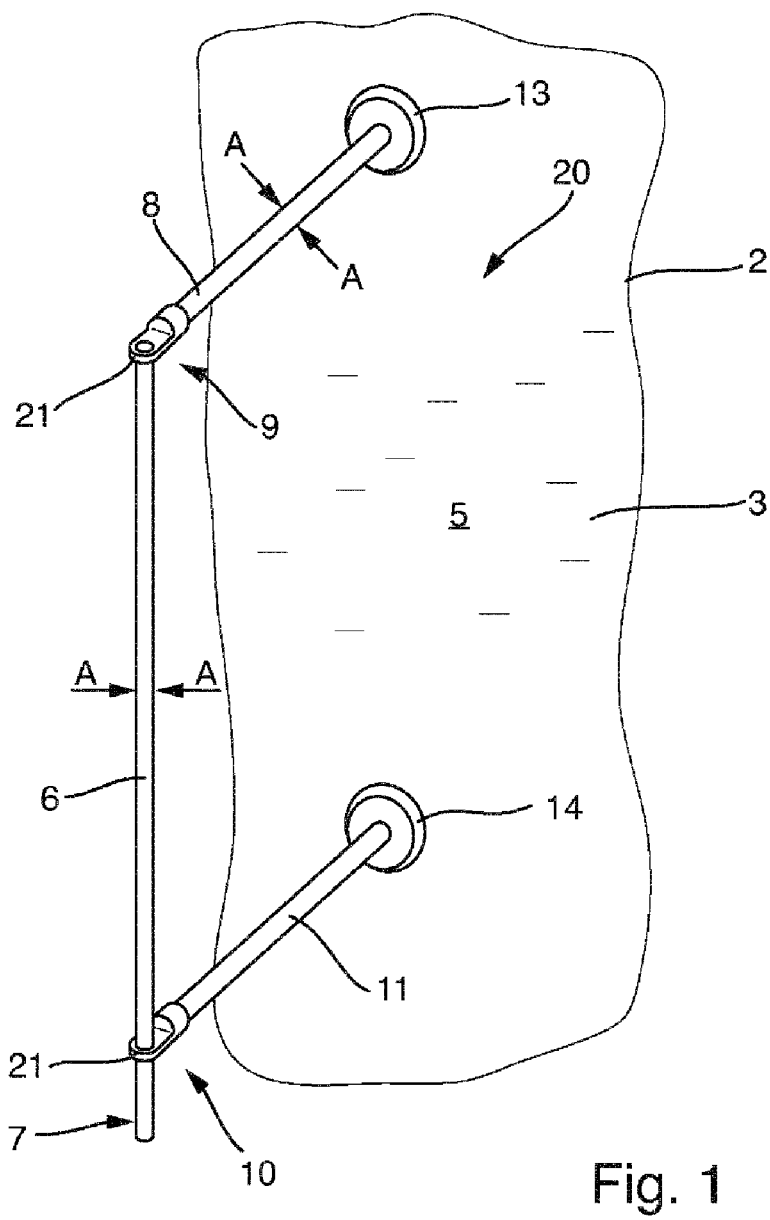
FIG. 1 shows a view of the inner wall of a container to which the device according to the present disclosure is fastened.
Figure 2:
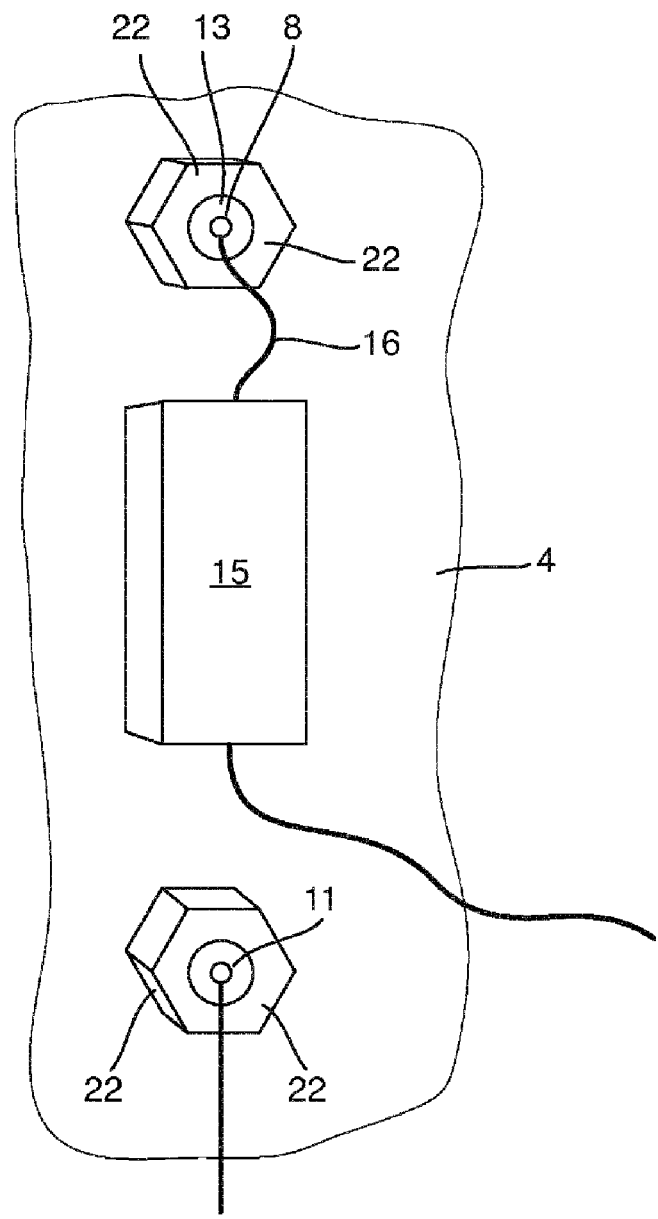
FIG. 2 shows a view of the outer wall of the embodiment of the device according to the present disclosure shown in FIG. 1.

The device according to the invention determines the moisture and/or conductivity of a medium 5 in any container 1 using a TDR method. FIGS. 1 and 2 schematically show a first embodiment of the device according to the invention which is located in the container 1 and fastened to the wall 2 of the container 1. FIG. 1 shows a perspective view of the inner wall 3 of the container 1, while FIG. 2 shows a perspective view of the outer wall 4 of the container 1.

In order to obtain reliable and accurate measurement results, it must be ensured when using a TDR method that an electrical pulse (or generally: a high-frequency measurement signal) generated by a signal processing unit 15 can propagate along a conductive element or a waveguide and that the pulse is reflected at the end of the waveguide and fed back into the signal processing unit. The conductivity and/or moisture of the medium 5 can be determined from the transit time of the pulse.

Essential components of the solution according to the invention are the signal processing unit 15, the measurement section consisting of the measurement line 8 and the measurement probe 6, and the non-conductive rod 11. In the embodiment shown, the device is fastened to the wall of a container 1. The container can be, for example, a tank, a silo or a pipeline. The container is made of metal or at least has a conductive material or at least a conductive coating on the inner wall 3 in the region of the device according to the invention. In order to avoid a short circuit between the conductive wall 2 of the container and the measuring device according to the invention, the measurement line 8 is fastened to the wall 2 of the container 1 by a non-conductive, insulating first feed-through 13 or fastening component. Depending on the temperature prevailing in the container, the first feed-through 13 or the first fastening component can consist, for example, of a plastic or of a heat-resistant ceramic. A second feed-through 14 or a second fastening component is provided for the non-conductive rod 11. Since the rod 8 is not electrically conductive, the second feed-through 14 may meet lower requirements than the first feed-through 13. The conductive and non-conductive rod are fastened, for example, by screw connections and nuts 22.

The measuring device according to the invention is fastened to the wall 2 of the container 1 by the conductive measurement line 8 and the non-conductive rod 11. The measurement line 8 is coupled to the upper end region 9 of the measurement probe 6, while the non-conductive rod 11 is connected to the lower end region 10 of the measurement probe 6. Fastening/connection is achieved by means of eyes 21. The measurement line 8 and the non-conductive rod 11 are arranged substantially at right angles to the wall 2 of the container 1 so that the measurement probe 6 is oriented substantially in parallel to the longitudinal axis of the container 1.

Here, as in the further embodiments of the device according to the invention shown, a pulse or a high-frequency measurement signal generated or triggered by the signal processing unit 15 passes through a cable 16 to the measurement line 8. The cable 16 is preferably a coaxial cable or a twisted wire. The coaxial cable and measurement line 8 are preferably matched to one another and coupled to one another in such a way that the high-frequency measurement signals are transmitted as losslessly as possible.

The pulse travels along the measurement probe 6 via the measurement line 8, is reflected at the free measurement probe end 7 and travels back in the direction of the signal processing unit 15. While the non-conductive rod 11 performs the function of an attachment to and a spacer from the wall 2 of the container 1, the measurement line 8 additionally performs the function of a waveguide for the electrical pulse or the high-frequency measurement signal.

The non-conductive rod 11 is advantageously designed as a glass fiber rod. This embodiment ensures a high break resistance. If high temperatures prevail in the container 1, the non-conductive rod 11 as well as the feed-throughs 13, 14 are made of temperature-resistant ceramic.

The outer diameter of the measurement line 8 and the measurement probe 6 are typically 10 mm. The same applies to the outer diameter of the non-conductive rod 11. Due to these relatively small dimensions, the device according to the invention represents only a relatively low flow resistance when installed in a container 1. This is important when the container 1 is filled with medium 5 or when the medium 5 is poured into the tank or into the silo and trickles or flows over the components of the measuring device in the container 1.

Since the TDR measuring field is substantially constructed between the measurement probe 6 or the measurement line 8 and a relatively large area of the conductive inner wall 3 of the container 1, it is guaranteed that the electrical impedance of the device according to the invention is relatively low. This has a positive effect on the impedance matching of the measurement signal transmitter, here the signal processing unit 15. As a result of the low impedance, the distance between the measurement probe 6 and the inner wall 3 can be selected to be relatively large. If the measurement probe 6 and the measurement line 8 have an outer diameter of 10 mm, for example, the measurement probe 6 can feasibly be a distance of, for example, 0.5 m to 1 m from the inner wall 3. Because the distance is large compared to the granularity of the medium 5, larger pieces of the medium, such as corn cobs, do not become wedged together between the measurement probe 6 or the two transverse struts 8, 11 and the inner wall 3 of the container 1.

This represents a considerable advantage of the solution according to the invention compared to known 2-rod probes or 3-rod probes, in which the measuring field is not formed between the waveguides and the inner wall 5 of the container 1 but between the rods of the measuring device. In order to achieve a suitably large measuring field in such cases, the spacing of the rods would have to be in the range of 0.5 m to 1 m. Since in many cases this is not a practical solution, the rods would alternatively need to have an outer diameter substantially larger than 10 mm. This would be the only way to reach comparably low impedance values. Rods with a large outer diameter, however, pose a problem, especially, in the case of temporary, i.e., shock-like mechanical loads when, for example, medium is fed in or out in large badges in a short time. The holders, too, must be designed to be suitably stable. Nevertheless, this does not avert the risk that a correspondingly massive probe may be torn out of the holder, the holder may be bent or the rods may be torn out of the probe head.

The device according to the invention can be designed particularly advantageously if the measurement line 8 and the measurement probe 6 as well as the non-conductive rod 11 are produced from a break-resistant and at the same time flexible carrier 17, especially, of one or more glass fibers. Such an embodiment of the components that protrude into the container 1 can react flexibly to mechanical loads. In the case of the rods 6, 8 which function as waveguides, the flexible carriers 17 or glass fibers are arranged in a thin-walled conductive tube 18.

Figure 3:
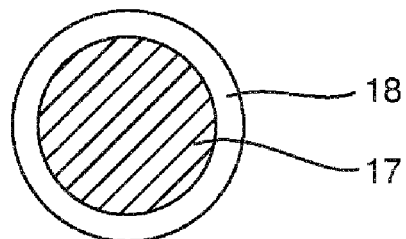
FIG. 3 shows a cross-section according to the label A-A in FIG. 1.

The measuring device according to the invention is break-resistant even when the container 1 is shock-loaded with tons of medium 5. The thin-walled metallic tube 18 can have, for example, a diameter of 10 mm and a tube wall thickness of 0.1 mm. When the rods 6, 8 are under a mechanical load as a result of a shock load, the thin-walled metallic tube 18 can be bent to a specified degree without breaking. After bending, the inner flexible glass fiber rod 17 ensures that the rods 6, 8 swing back to their original position again and thus do not bend permanently. The glass fiber rod 11 from which the non-conductive rod 11 is formed also responds the same way. A cross-section through a conductive rod 6, 8 having an inner carrier 17 or at least one inner glass fiber 17 (see label A-A in FIG. 1) can be seen in FIG. 3.

The installation/attachment of the single-rod probe according to the invention on/to a metal wall 2 of a container 1 is advantageous in many applications, such as in a silo. It has already been mentioned that the TDR measuring field in the solution according to the invention is constructed between the measurement line 8, the measurement probe 6 and the electrically conductive surface 20 of the wall 2, which is influenced by the measuring field. As a result, the impedance of the device according to the invention is relatively low, which has a positive effect on the impedance matching of signal processing unit 15 and measurement line 6, 8. It is necessary, however, to provide corresponding openings in the container, in which openings the feedthroughs 13, 14 and the measuring device are fastened. This is quite complex.

If there are defects in the device according to the invention, the components protruding into the container and the components arranged outside the container 1 must always be replaced separately from one another for repair or replacement. In addition, the length of the cable 16 or of the coaxial cable 16 which leads from the signal processing unit 15 to the measurement line 8 is also problematic when connecting replacement components, since the cable length plays an important role in the transit time measurement of the TDR pulse. If components of the device according to the invention are replaced, it is therefore not possible to avoid having to recalibrate the device. Hence, there are definitely applications in which a plug-and-play solution is preferable.

Furthermore, there are applications in which mounting the single-rod probe on a wall 2 of a container 1 entails problems. Problems especially occur if the temperature in the region of the wall 2 of the container is different from the temperature prevailing in the interior of the container 1. Silos are often found in the open air, meaning that silos heat up in summer and cool off in winter in the region of the metal wall 2. The installation of a single-rod probe in the middle of a container 1 or of a silo therefore has advantages in corresponding applications.

Figures 4, 5:
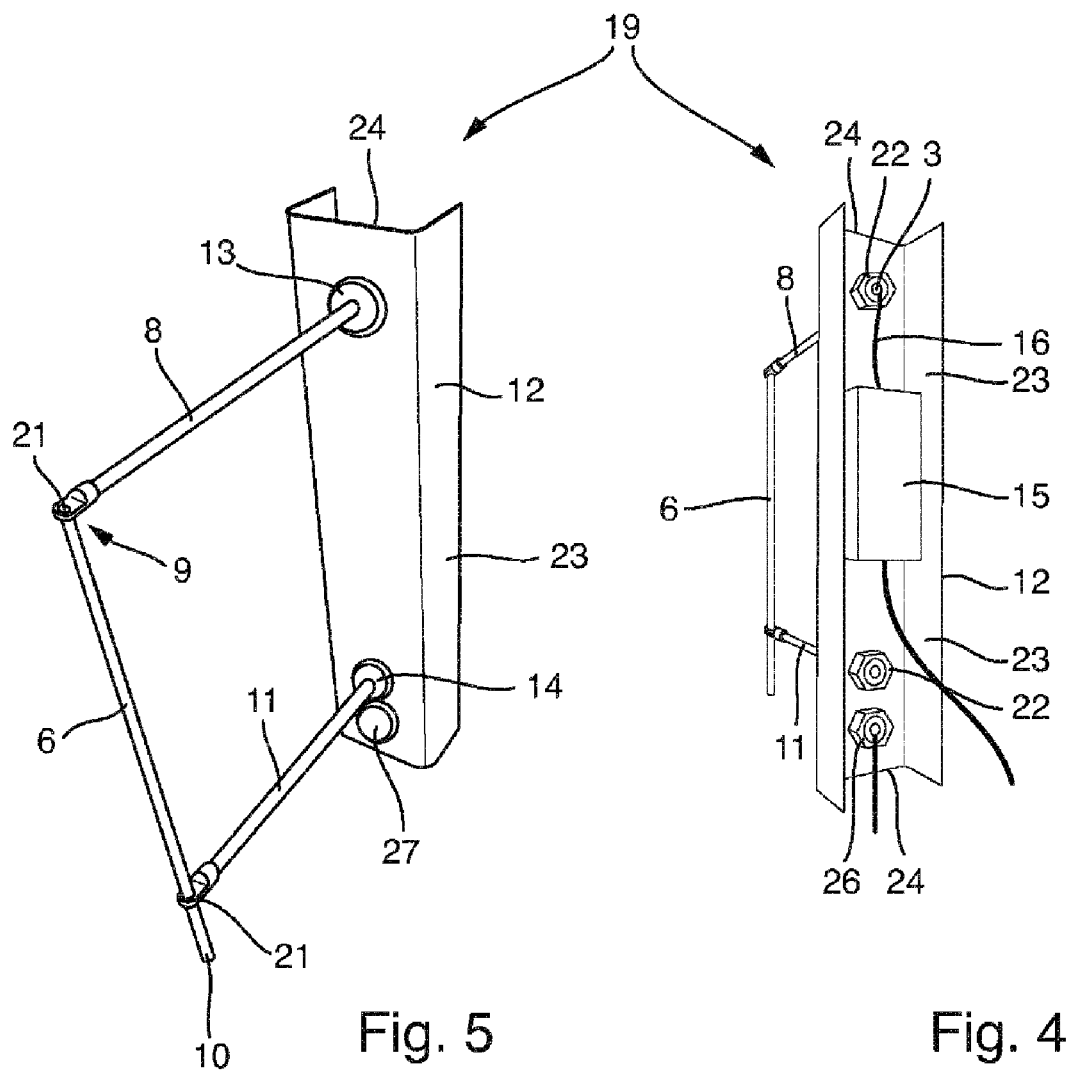
FIG. 4 shows a front perspective view of a second embodiment of the device according to the present disclosure which is fastened to a holder.
FIG. 5 shows a rear perspective view of the second embodiment of the device according to the present disclosure shown in FIG. 4.

FIGS. 4 and 5 show a second embodiment of the device according to the invention in perspective views. FIG. 4 shows a view of the "front" of the device according to the invention, FIG. 5 a view of the "back" of the device according to the invention. This embodiment describes a compact version of the device according to the invention.

The difference from the embodiment described above is substantially that the fastening of the device for measuring the moisture and/or conductivity of a medium 5 is not fastened in/on the wall 2 of the container 1 but on a metal housing or a holder 23, here a U-shaped metal housing. The signal processing unit 15 is installed in the U-shaped housing 23, which is closed on three sides, while the measurement lines 8, 6 are mounted outside on the central wall of the U-shaped housing 23. This arrangement has the great advantage that the device according to the invention can be treated as an integrated and thus also easily replaceable single-rod probe 19. This is of particular advantage for installation, start-up, and servicing.

In addition, there are applications in which the moisture/ conductivity of a medium 5 must be measured at different heights within a container 1. When the medium 5 is stored or dried, the moisture/conductivity can depend on the height of the medium 5 in the container 1.

Figure 6:
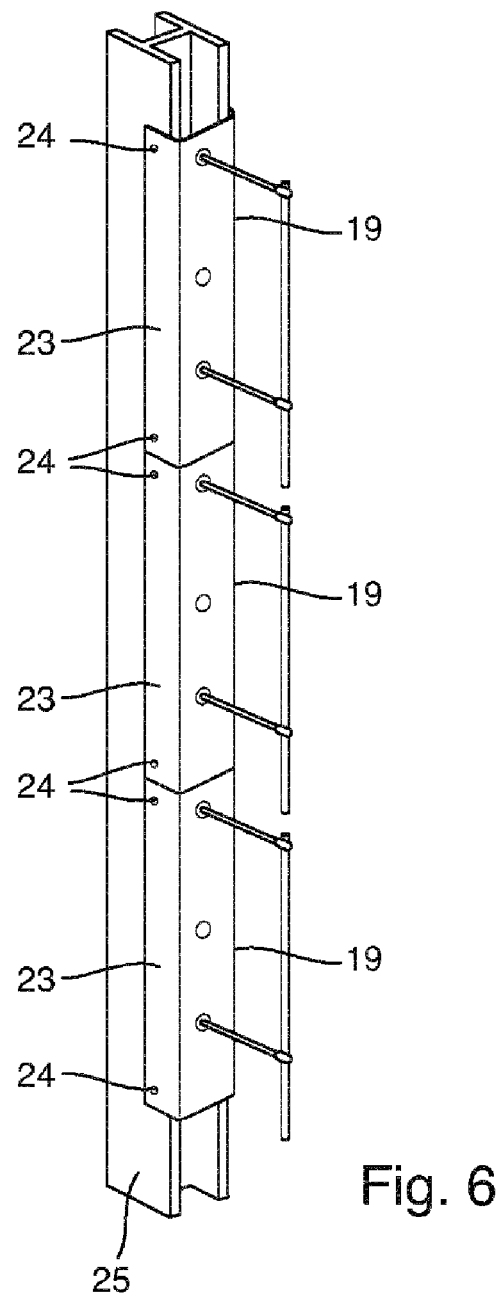
FIG. 6 shows a perspective view of a third embodiment of the device according to the present disclosure.

Knowledge about the moisture profile of the medium 5 in a container 1 is quite important here: If the moisture differences in the medium 5 are known, the vertical hot air flow can be switched from bottom to top or from top to bottom within the container 1 by means of a drying device. This ensures that the medium 5 is dried evenly. A cascaded and vertically constructed arrangement of a plurality of preferably integral devices 19 according to the invention within the container 1 has the advantage that the moisture can be determined in a plurality of material layers. An embodiment of the solution according to the invention suitable for the application described above is shown in FIG. 6 in perspective view.

Due to high mechanical loads during filling and emptying of a container 1 or silo, the holders (the holders are not shown separately in FIG. 6) must be designed to be highly mechanically stable for a plurality of cascaded single-rod probes. A rail 25 formed as an H-beam or I-beam and anchored to the floor and to the ceiling of the container 1 in a stable manner by holders is, for example, ideally suited for receiving the U-shaped housing 23. Corresponding anchors are known to the person skilled in the art. The dimensioning of the side surfaces of the U-shaped housing and of the corresponding surfaces of the H- or I-beam is selected such that the signal processing unit 15 has sufficient space inside the U-shaped housing 23 when said housing is pushed over the rail 25 or over the H- or I-beam. The U-shaped housing 23 is fastened to the rail 25 by bores 27 and matching fastening elements.

Figure 7:
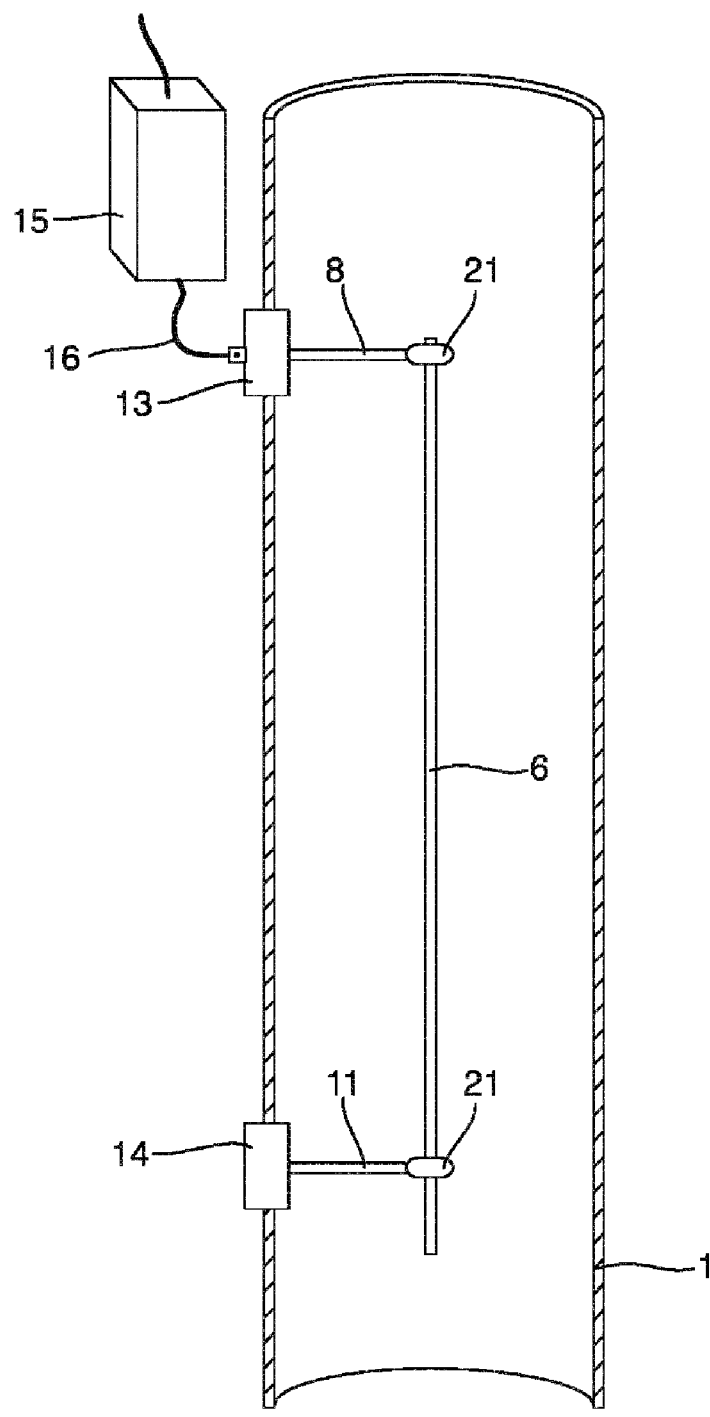
FIG. 7 shows a schematic representation of a fourth embodiment of the device according to the present disclosure which is fastened in a pipeline.

There are also applications in which the moisture or water content in a low-density medium 5 must be measured. The medium 5 is, for example, hot steam or a gas. For such applications, it is advantageous if the single-rod probe according to the invention is installed directly in a pressurized metal pipe 1 through which the medium 5 to be measured flows. FIG. 7 shows a longitudinal section of a fourth embodiment of the device according to the invention, which is mounted in a pipeline 1 or a pipeline section 1.

Here, the rod arrangement 6, 8, 11 is attached in the interior, for example, preferably in the central region of the metal pipeline 1, so that the measurement probe 6 is aligned along the longitudinal axis of the pipeline 1. The structure is therefore comparable to the structure of a coaxial cable. The electrical measuring field of the TDR signal is constructed between the single-rod probe 6, 8 and the inner metal surface of the pipe 1. The break-resistant design of the rod arrangement has a positive effect on possible pressure surges occurring in the pipeline 1. In high-temperature applications, insulating components 13, 11, 14 of the single-rod probe are made of ceramic rather than plastic.

LIST OF REFERENCE SIGNS

1 Container, tank, silo, pipeline
2 Wall
3 Inner wall
4 Outer wall
5 Medium
6 Measurement probe
7 Measurement probe end
8 Measurement line/conductive rod
9 Upper end region of measurement probe
10 Lower end region of measurement probe
11 Non-conductive rod
12 Elongate holder
13 First feed-through/first fastening component
14 Second feed-through/second fastening component
15 Signal processing unit
16 Cable
17 Flexible carrier
18 Conductive tube
19 Compact unit, integrated single-rod probe
20 Conductive surface of the container
21 Eye
22 Nut
23 Holder/U-shaped rail
24 Fastening means
25 Rail/I- or H-shaped rail
26 Temperature sensor
27 Bore

The invention claimed is:

1. A device for determining the moisture or the conductivity of a flowable medium in a container, comprising a measurement probe of a specified length which is plunged into the medium and consists of a conductive material,
wherein a measurement line designed as a conductive rod is provided in the upper end region of the measurement probe,
wherein a first feed-through or a first fastening component is provided, which is designed in such a way that the measurement line designed as a conductive rod can be fastened, in an electrically insulated manner, to an electrically conductive wall of the container or to an electrically conductive elongate holder,
wherein a rod of a non-conductive material is provided in the lower end region of the measurement probe,
wherein a second feed-through or a second fastening component is provided, which is designed in such a way that the non-conductive rod can be fastened to the wall of the container or to the elongate holder,
wherein the conductive rod and the non-conductive rod are dimensioned and oriented such that the measurement probe, when mounted, is oriented substantially in parallel to the longitudinal axis of the container or the elongate holder, and
wherein a signal processing unit is provided which is designed such that high-frequency measurement signals are conducted via the measurement line to the measurement probe and the moisture or conductivity of the medium is determined by means of a TDR method;
wherein the measurement probe and the conductive rod designed as a measurement line consisting of a flexible carrier, wherein the flexible carrier is surrounded by a thin-walled, electrically conductive tube or by an electrically conductive coating or by an electrically conductive shrink tube;
wherein the non-conductive rod is designed as a flexible glass fiber rod.

2. The device of claim 1, wherein the measurement line designed as a conductive rod and the non-conductive rod have a length which is dimensioned such that a measuring field for the high-frequency measurement signal is constructed between the conductive rod, the measurement probe and the adjoining surface of the inner wall of the container or holder.

3. The device of claim 1, wherein the thickness of the thin-walled, electrically conductive tube or of the electrically conductive coating or of the electrically conductive shrink tube is in the range of 0.5 to 2.5 mm, and wherein the outer diameter of the thin-walled, electrically conductive tube or of the electrically conductive coating or of the electrically conductive shrink tube is between 5 and 15 mm.

4. The device of claim 1, wherein the conductive rod designed as a measurement line and the non-conductive rod have a length between 0.3 and 3 m.

5. The device of claim 1, wherein the first feed-through or the first fastening component and the second feed-through or the second fastening component consist of an insulating plastic or of an insulating ceramic.

6. The device of claim 1, wherein a cable is provided, by which the signal processing unit is electrically connected to the end region of the measurement line designed as a conductive rod.

7. The device of claim 1, wherein the holder is designed as a rail, wherein the measurement probe is arranged on the outer surface of the central section of the rail, and wherein the signal processing unit is arranged on the inner surface of the central section of the rail.

8. The device of claim 1, wherein the holder and the conductive rod and the measurement probe form a compact unit.

9. The device of claim 8, wherein a plurality of the compact units are attached to an elongate rail in a cascade.

10. The device of claim 9, wherein fasteners for fastening the rail to a floor and to a cover of the container are provided in the end regions of the elongate rail.

11. The device of claim 9, wherein each compact unit includes or is in communication with a temperature sensor.

12. The device of claim 1, wherein the container, which is metallic or electroconductive at least on the inner surface, is configured as a pipeline section and wherein the single-rod probe is installed in the pipeline section.

* * * * *